US010143623B2

(12) United States Patent
Suzuki et al.

(10) Patent No.: US 10,143,623 B2
(45) Date of Patent: Dec. 4, 2018

(54) SYRINGE CONTAINER

(71) Applicants: Kazuo Suzuki, Tokyo (JP); Hiroyuki Nakamura, Tokyo (JP)

(72) Inventors: Kazuo Suzuki, Tokyo (JP); Hiroyuki Nakamura, Tokyo (JP)

(73) Assignee: YOSHINO KOGYOSHO CO., LTD., Tokyo (JP)

( * ) Notice: Subject to any disclaimer, the term of this patent is extended or adjusted under 35 U.S.C. 154(b) by 5 days.

(21) Appl. No.: 15/328,826

(22) PCT Filed: Aug. 6, 2015

(86) PCT No.: PCT/JP2015/072406
§ 371 (c)(1),
(2) Date: Jan. 24, 2017

(87) PCT Pub. No.: WO2016/067705
PCT Pub. Date: May 6, 2016

(65) Prior Publication Data
US 2017/0216141 A1 Aug. 3, 2017

(30) Foreign Application Priority Data

Oct. 31, 2014 (JP) .................................. 2014-223599

(51) Int. Cl.
| | |
|---|---|
| *A61J 1/20* | (2006.01) |
| *B65D 51/32* | (2006.01) |
| *B65D 53/02* | (2006.01) |
| *A61M 5/31* | (2006.01) |
| *A61M 5/315* | (2006.01) |
| *A61M 5/32* | (2006.01) |
| *B01L 3/02* | (2006.01) |
| *A61M 5/24* | (2006.01) |

(52) U.S. Cl.
CPC .............. *A61J 1/20* (2013.01); *A61J 1/2003* (2015.05); *A61M 5/315* (2013.01);
(Continued)

(58) Field of Classification Search
CPC .... A61J 1/20; A61M 5/3148; A61M 5/31583; A61M 5/315; A61M 5/3129; A61M 5/3202; A61M 2005/2488
See application file for complete search history.

(56) References Cited

U.S. PATENT DOCUMENTS

2011/0284123 A1 11/2011 Bouix et al.

FOREIGN PATENT DOCUMENTS

| | | |
|---|---|---|
| CN | 103002855 A | 3/2013 |
| CN | 203493018 U | 3/2014 |

(Continued)

OTHER PUBLICATIONS

Dec. 5, 2017 Office Action issued in Chinese Patent Application No. 201580046182.9.

(Continued)

*Primary Examiner* — Amber Stiles
(74) *Attorney, Agent, or Firm* — Oliff PLC

(57) ABSTRACT

According to the present invention, a packing member (20) is disposed between a mouth portion (2b) of a container body (2) and a lid base portion (5). A crushing protrusion (20b) which protrudes downward and is crushed to an upper end opening edge of the container body (2) is formed on a lower surface of the packing member (20). An overhang recess (20c) which is at least partially located just above the crushing protrusion (20b) is formed on an upper surface of the packing member (20). After the lid base portion (5), the movable lid portion (6) and the syringe tube (8) are detached from the container body (2), when mounting again, until a crushing protrusion (20b) is crushed, the packing member (20) forms a communication gap (30) between the mouth portion (2b) of the container body (2) and the packing member (20).

8 Claims, 5 Drawing Sheets

(52) U.S. Cl.
CPC ........ *A61M 5/3129* (2013.01); *A61M 5/3148* (2013.01); *A61M 5/31583* (2013.01); *A61M 5/3202* (2013.01); *B01L 3/021* (2013.01); *B01L 3/0241* (2013.01); *B65D 51/32* (2013.01); *B65D 53/02* (2013.01); *A61M 2005/2488* (2013.01); *B01L 2200/0605* (2013.01); *B01L 2300/042* (2013.01); *B01L 2300/047* (2013.01); *B01L 2400/0478* (2013.01); *B01L 2400/0481* (2013.01)

(56) References Cited

FOREIGN PATENT DOCUMENTS

| | | |
|---|---|---|
| EP | 0 701 865 A1 | 3/1996 |
| JP | H02-131959 U | 11/1990 |
| JP | H06-42735 Y2 | 11/1994 |
| JP | H07-33157 A | 2/1995 |
| JP | H07-17757 U | 3/1995 |
| JP | H07-26366 U | 5/1995 |
| JP | H08-84934 A | 4/1996 |
| JP | 2000-095261 A | 4/2000 |
| JP | 2013-533172 A | 8/2013 |
| JP | 2013-538756 A | 10/2013 |
| WO | 2011/149652 A2 | 12/2011 |
| WO | 2011/154397 A1 | 12/2011 |

OTHER PUBLICATIONS

Oct. 27, 2015 International Search Report issued in International Patent Application No. PCT/JP2015/072406.
May 11, 2018 Extended European Search Report Issued in European Patent Application No. 15854713.3.

SYRINGE CONTAINER

TECHNICAL FIELD

The present invention relates to a syringe container.

Priority is claimed on Japanese Patent Application No. 2014-223599, filed Oct. 31, 2014, the content of which is incorporated herein by reference.

BACKGROUND ART

As a syringe container, as described in Patent Document 1, a configuration including a container body having a mouth portion, and a cap with syringe mounted to the mouth portion is known. The cap with syringe has a lower half of a syringe tube which is inserted into the container body through the mouth portion. In the upper end portion of the syringe tube, an elastic dome body, and a press-down cylinder for pressing down the elastic dome body are provided. In the syringe container, because contents of the container body are sucked up the by pressing down the press-down cylinder to press the elastic dome body, a suction amount of the contents easily changes depending on the press-down amount of press-down cylinder.

Here, in this type of syringe container, it is desired to accurately suck up and eject a certain amount of liquid depending on the type of contents.

Thus, for example, a syringe container as described in Patent Document 2 has also been suggested. The syringe container is equipped with a lid base portion disposed on a mouth portion of the container body, and a movable lid portion that is disposed to be freely movable upward to the lid base portion. Between the lid base portion and the movable lid portion, a pump chamber for generating a negative pressure communicating with the syringe tube is formed. In the syringe container, when raising and disengaging the movable lid portion from the mouth portion, by generating a negative pressure in the pump chamber in accordance with the raising distance of the movable lid portion, the liquid of the container body is sucked up to the interior of the syringe tube.

DOCUMENT OF RELATED ART

Patent Literature

[Patent Document 1]
Japanese Unexamined Patent Application, First Publication No. H6-42735
[Patent Document 2]
Published Japanese Translation No. 2013-533172 of the PCT International Publication

SUMMARY OF INVENTION

Technical Problem

However, in the conventional syringe container, even when the magnitude of the negative pressure generated in the pump chamber with the rise of the movable lid portion is constant, the suction amount of the contents may change in accordance with the remaining amount of the contents of the container body. Thus, there is room for improvement for keeping the suction amount constant with high precision, regardless of the remaining amount of the contents.

The present invention has been made in view of the aforementioned circumstances, and an object thereof is to provide a syringe container in which the suction amount is kept constant with high precision, regardless of the remaining amount of the contents.

Solution to Problem

A syringe container according to an aspect of the present invention includes a container body which stores contents; a lid base portion which is disposed on a mouth portion of the container body; a movable lid portion which is disposed to freely move upward with respect to the lid base portion; an urging means which urges the lid base portion and the movable lid portion in a vertically separating direction; and a syringe tube which is mounted on the lid base portion and extends toward the container body, the movable lid portion including a mounting cylinder which is mounted on the mouth portion of the container body in a freely attachable and detachable manner, a lid which is formed to be elastically deformable and closes the upper end opening of the mounting cylinder, and a cylinder portion which is disposed inside the mounting cylinder in a radial direction and is connected to the mounting cylinder, the lid base portion including a piston portion which is connected to the syringe tube and fitted to the inside of the cylinder portion to freely slide up and down, the cylinder portion being mounted on the syringe tube to freely rise, the cylinder portion and the syringe tube are formed with engaging portions which engage with each other when the cylinder portion is located at a rising end position with respect to the syringe tube, the interior of the syringe tube communicating with a space between the upper end opening of the mounting cylinder and the lid, and the cylinder portion having a communication hole formed therein through which the interior and the space communicate with each other. Further, a packing member is disposed between the lid base portion and the upper end opening edge of the mouth portion of the container body, and a crushing protrusion is formed on the lower surface of the packing member, the crushing protrusion protruding downward and being crushed against the upper end opening edge of the container body, and an overhang recess is formed on the upper surface of the packing member, the overhang recess being at least partially located just above the crushing protrusion.

In this case, first, in order to disengage the syringe tube from the container body, the movable lid portion is raised with respect to the container body. Next, due to the urging force of the urging means, the piston portion of the lid base portion slides relatively downward inside the cylinder portion of the movable lid portion, the internal volume of the cylinder portion increases, and a negative pressure is generated in the cylinder. The negative pressure is exerted on the interior of the container body through the communication hole, the space and the syringe tube, and the contents in the container body are sucked into the syringe tube. After the movable lid portion rises to the rising end position with respect to the syringe tube and the engaging portions engage with each other, when further raising the movable lid portion with respect to the container body, the movable lid portion and the syringe tube rise together through the engagement, and thus, the syringe tube, the movable lid portion and the lid base portion are detached from the container body. Further, by pressing the lid, the contents of the syringe tube are dispensed from the lower end opening of the syringe tube.

According to the syringe container, after the movable lid portion is detached from the container body and the contents of the syringe tube are spouted from the lower end opening of the syringe tube as described above, when the syringe tube is inserted into the container body again, the movable lid portion is mounted on the container body, and the movable lid portion is lowered to the lid base portion, the piston portion of the lid base portion slides relatively upward inside the cylinder portion of the movable lid portion to reduce the internal volume of the cylinder portion and generate a positive pressure in the cylinder portion.

At this time, although the packing member is disposed between the lid base portion and the upper end opening edge of the mouth portion of the container body, because the crushing protrusion protruding downward is formed on a lower surface of the packing member, a communication gap through which the inside and outside of the container body communicate with each other due to the crushing protrusion is formed between the lid base portion and the upper end opening edge of the container body. Thus, the positive pressure generated in the cylinder portion is released outside of the container body through the communication hole, the space, the syringe tube and the container body, and an internal pressure rise in the container body can be minimized.

Thereafter, by further lowering the movable lid portion, the packing member is pressed between the lid base portion and the upper end opening edge of the container body, and in particular, the crushing protrusion is crushed to the upper end opening edge of the container body. At which time, since the overhang recess is formed just above the crushing protrusion, the deformation of the crushing protrusion to the upper surface side is allowed by the overhang recess. Accordingly, the crushing of the crushing protrusion toward the upper side smoothly occurs without great resistance. Accordingly, sealing properties between the upper end opening edge of the lid base portion and the container body provided by the packing member are satisfactorily ensured.

In the above syringe container, the packing member may have a locking protrusion formed therein which is locked to an outer circumferential surface of the upper end opening of the mouth portion of the container body.

In this case, after dispensing from the syringe tube, when the movable lid portion is mounted on the container body again and the movable lid portion is lowered, the displacement of the packing member to the inside of the container body caused by being crushed between the lid base portion and the upper end opening edge of the container body is suppressed by the locking protrusion which engages with the outer circumferential surface of the upper end opening of the container body.

The mounting cylinder may be screwed into the mouth portion, and may be connected to the cylinder portion via a connection, and the lid base portion may engage with the connection when the mounting cylinder rotates about the container axis, and may rotate with the movable lid portion.

In this case, when the mounting cylinder rotates about the container axis, since the lid base portion engages with the connection and rotates with the movable lid portion, when attaching and detaching the mounting cylinder to and from the mouth portion of the container body, the lid base portion as well as the movable lid portion can also rotate, and the piston portion can be caused to smoothly vertically slide inside the cylinder portion.

The movable lid portion includes an external cylinder which is mounted on the mounting cylinder to be relatively vertically immovable and non-rotatable from the outside in the radial direction, and the external cylinder may expose the lid upward, while interposing a circumferential edge portion of the lid in the vertical direction between the mounting cylinder and the external cylinder.

In this case, since the external cylinder exposes the lid upward, while sandwiching the circumferential edge portion between the mounting cylinder and the external cylinder in the vertical direction, the lid can be firmly fixed to the mounting cylinder, without impeding the pressing operation of the lid.

Effects of Invention

According to the present invention, it is possible to keep the suction amount constant with high precision, regardless of the remaining amount of the contents.

DESCRIPTION OF EMBODIMENTS

First Embodiment

Hereinafter, a syringe container according to a first embodiment of the present invention will be described with reference to accompanying drawings.

Figure 1:
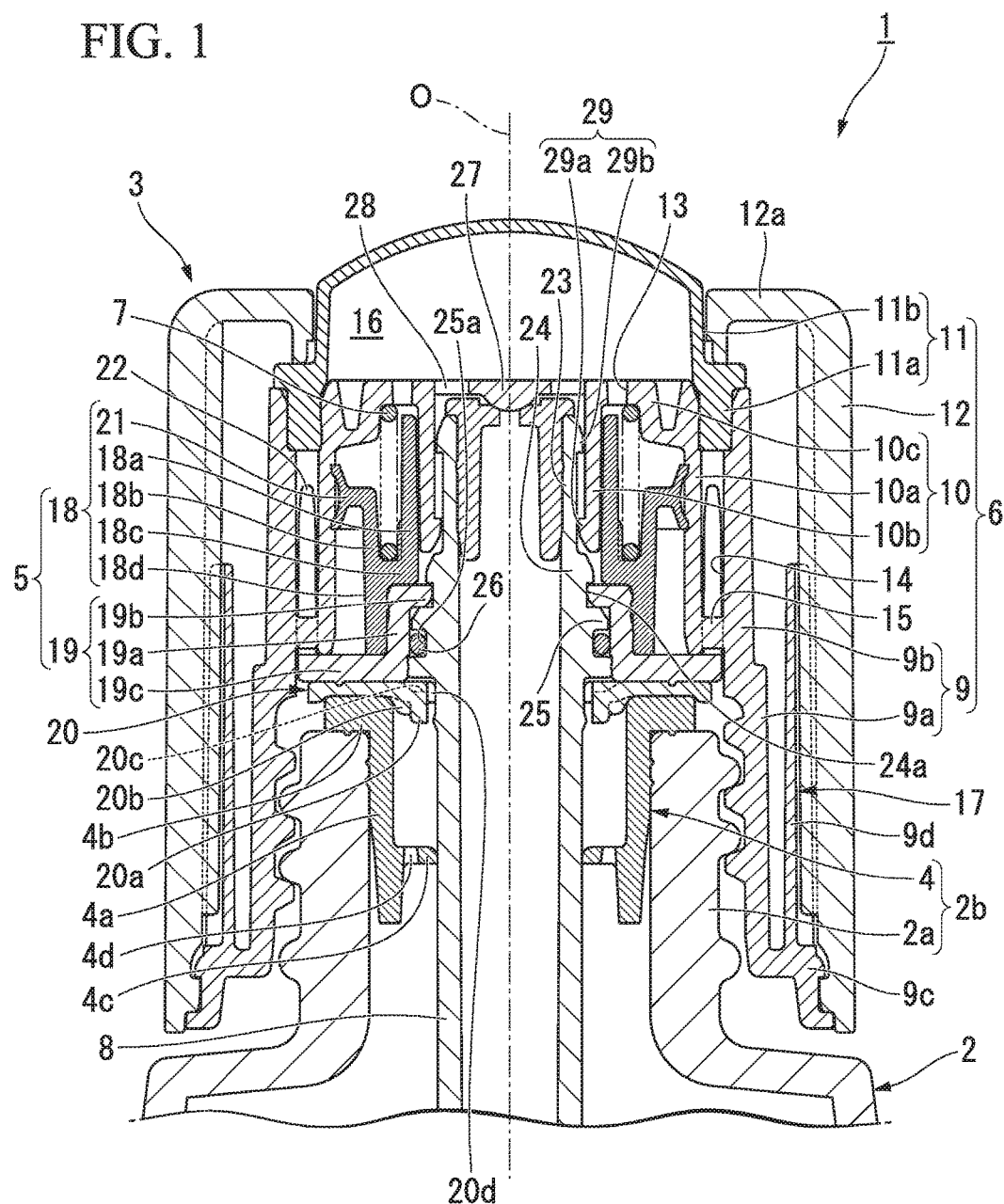
FIG. 1 is a vertical sectional view of main parts of a syringe container according to a first embodiment of the present invention, showing an initial state.

FIG. 1 is a vertical sectional view of main parts showing a schematic configuration of a syringe container according to the first embodiment of the present invention, showing an initial state in which the movable lid portion is closed. A syringe container 1 shown in FIG. 1 includes a container body 2 that stores contents, and a syringe cap 3 that is mounted to the container body 2 in a freely attachable and detachable manner.

The container body 2 is formed in a bottomed cylindrical shape, and each central axis of the container body 2 and a syringe tube 8 to be described later of the syringe cap 3 is disposed on a common axis. Hereinafter, the common axis is defined as a container axis O, a direction along the container axis O is defined as a vertical direction, a bottom side of the container body 2 along the vertical direction is defined as a lower side, and a mouth portion side of the container body 2 as the opposite side thereto is defined as an upper side. In a plan view in which the syringe container 1 is viewed in the vertical direction, a direction orthogonal to the container axis O is defined as a radial direction, and a direction going around the container axis O is defined as a circumferential direction.

The container body 2 is provided with a guide cylinder 4 which is fixed by being mounted to the mouth portion body 2a which is formed integrally with a body portion or a bottom portion by press-fitting or the like. Thus, the mouth portion 2b of the container body 2 is formed to include the mouth portion body 2a and the guide cylinder 4. The guide cylinder 4 includes a cylindrical main cylinder portion 4a inserted into the upper end portion of the mouth portion body 2a, an annular disk-shaped flange portion 4b which extends radially outward from the upper end of the main cylinder portion 4a and locks to an upper end opening edge of the mouth portion body 2a, and a wiping piece 4c which protrudes radially inward from the inner surface of the main cylinder portion 4a. The wiping piece 4c vertically and slidably comes into contact with the outer circumferential surface of a syringe tube 8 to be described later to wipe off the contents adhering to the outer circumferential surface of the syringe tube 8. The wiping piece 4c is connected to the main cylinder portion 4a via connecting pieces 4d. A plurality of connecting pieces 4d are disposed at intervals in the circumferential direction. Further, the guide cylinder 4 may also be formed integrally with the container body 2.

The syringe cap 3 includes a lid base portion 5 disposed on the mouth portion 2b of the container body 2, a movable lid portion 6 which is disposed to be freely movable upward with respect to the lid base portion 5, an urging means 7 which urges the lid base portion 5 and the movable lid portion 6 in a direction of vertically separating the lid base portion 5 and the movable lid portion 6, a syringe tube 8 which is mounted to the lid base portion 5 and extends toward the container body 2, and a packing member 20.

The movable lid portion 6 includes a mounting cylinder 9, a cylinder portion 10, a lid 11, and an external cylinder 12. Both of the cylinder portion 10 and the lid 11 are formed in a cylindrical shape. All of the mounting cylinder 9, the cylinder portion 10, the lid 11 and the external cylinder 12 are disposed coaxially with the container axis O.

The mounting cylinder 9 is mounted to the mouth portion body 2a of the container body 2 in a freely attachable and detachable manner. In the present embodiment, a lower portion 9a of the mounting cylinder 9 is screwed into the mouth portion body 2a from the outside in the radial direction, and an upper portion 9b protrudes upward from the mouth portion body 2a. In the lower end portion of the mounting cylinder 9, a flange portion 9c protruding outward in the radial direction is provided. An engagement cylinder 9d that is disposed coaxially with the container axis O, and surrounds the mounting cylinder 9 from the outside in the radial direction, is erected on the flange portion 9c.

The cylinder portion 10 is disposed inside the mounting cylinder 9 in the radial direction and is connected to the mounting cylinder 9. The cylinder portion 10 is disposed in the upper portion 9b of the mounting cylinder 9. The cylinder portion 10 is formed in a double cylindrical shape, and includes an outer circumferential wall 10a, an inner circumferential wall 10b, and a top wall portion 10c. The outer circumferential wall 10a is formed to have a size equivalent to the upper portion 9b of the mounting cylinder 9 in the vertical direction, and the inner circumferential wall 10b is formed to be smaller than the outer circumferential wall 10a in the vertical direction. Upper end portions of both the outer circumferential wall 10a and the inner circumferential wall 10b are disposed at equivalent positions in the vertical direction. The top wall portion 10c is formed in an annular shape coaxial with the container axis O to connect the respective upper end portions of the outer circumferential wall 10a and the inner circumferential wall 10b.

Communication holes 13, which penetrate the top wall portion 10c in the vertical direction, are formed in the top wall portion 10c. A plurality of communication holes 13 are provided at intervals in the circumferential direction. The communication holes 13 communicate with the interior of the cylinder portion 10 that is formed by the outer circumferential wall 10a, the inner circumferential wall 10b and the top wall portion 10c.

An annular gap 14 is provided between the mounting cylinder 9 and the cylinder portion 10. The annular gap 14 is formed between the upper portion 9b of the mounting cylinder 9 and the outer circumferential wall 10a of the cylinder portion 10.

The mounting cylinder 9 and the cylinder portion 10 are connected to each other via the connection 15. A plurality of connections 15 are provided in the annular gap 14 at intervals in the circumferential direction to intermittently connect the lower end portion of the upper portion 9b of the mounting cylinder 9 and the lower end portion of the outer circumferential wall 10a of the cylinder portion 10. Thus, the cylinder portion 10 moves integrally with the mounting cylinder 9.

The lid 11 is formed to be elastically deformable to close the upper end opening of the mounting cylinder 9. The lid 11 is formed in a topped cylinder shape (a dome shape), and includes a fitting cylindrical portion 11a, and a film cylinder portion 11b. The fitting cylindrical portion 11a is air-tightly fitted into the upper end portion of the annular gap 14. The film cylinder portion 11b is formed in a topped cylinder shape, and protrudes upward from the inner circumferential edge of the fitting cylindrical portion 11a, and a top portion thereof is formed in a dome shape.

Between the upper end opening of the mounting cylinder 9 and the film cylinder portion 11b of the lid 11, a space 16 that communicates with the interior of the cylinder portion 10 through the communication hole 13 is provided.

The external cylinder 12 is mounted to the mounting cylinder 9 from the outside in the radial direction to be relatively vertically immovable and non-rotatable. The external cylinder 12 is mounted to be vertically immovable, by being undercut-fitted to the flange portion 9c of the mounting cylinder 9. Rotation restricting portions 17 are provided between the external cylinder 12 and the engagement cylinder 9d of the mounting cylinder 9, respectively. The rotation restricting portions 17 restrict relative rotational movement between the external cylinder 12 and the engagement cylinder 9d in the circumferential direction by engaging with each other. The external cylinder 12 is non-rotatable with respect to the mounting cylinder 9, due to the rotation restricting portions 17.

The external cylinder 12 exposes the lid 11 upward, while interposing its circumferential edge portion in the vertical direction between the mounting cylinder 9 and the external cylinder 12. A restricting ring 12a protruding inward in the radial direction is provided at the upper end portion of the external cylinder 12, and between the inner circumferential edge portion of the restricting ring 12a and the upper end portion of the mounting cylinder 9, the fitting cylindrical portion 11a of the lid 11 is interposed in the vertical direction. A film cylinder portion 11b of the lid 11 is disposed inside the restricting ring 12a, and the top wall portion of the film cylinder portion 11b bulges upward from the restricting ring 12a.

The lid base portion 5 is provided with a piston portion 18 and a piston support portion 19. Further, in this embodiment, a packing member 20 is mounted to the piston support portion 19 of the lid base portion 5. Both of the piston portion 18 and the piston support portion 19 are formed in a cylindrical shape, and the packing member 20 is formed in an annular shape. The piston portion 18, the piston support portion 19 and the packing member 20 are disposed coaxially with the container axis O.

The piston portion 18 is fitted into the cylinder portion 10 to be freely relatively vertically slidable. The piston portion 18 includes an internal cylinder portion 18a, an external cylinder portion 18b, a bottom wall portion 18c, and a leg cylinder portion 18d.

The internal cylinder portion 18a is fitted to the inner circumferential wall 10b of the cylinder portion 10 to be freely vertically rotatable from the outer side in the radial direction. The external cylinder portion 18b surrounds the internal cylinder portion 18a from the outer side in the radial direction. The external cylinder portion 18b is smaller than the internal cylinder portion 18a in the vertical direction, and each of the lower end portions of the external cylinder portion 18b and the internal cylinder portion 18a are disposed at equivalent positions in the vertical direction. A sliding portion 21 protruding inward in the radial direction is provided at the upper end portion of the external cylinder portion 18b. The sliding portion 21 is fitted into the outer circumferential wall 10a of the cylinder portion 10 to be freely vertically slidable. The bottom wall portion 18c is formed in an annular shape coaxial with the container axis O to connect the respective lower end portions of the internal cylinder portion 18a and the external cylinder portion 18b. The leg cylinder portion 18d extends downward from the external cylinder portion 18b.

The piston support portion 19 includes a base cylinder portion 19a, an annular plate portion 19b, and a substrate portion 19c. The base cylinder portion 19a is fitted into the leg cylinder portion 18d of the piston portion 18. The annular plate portion 19b protrudes inward in the radial direction from the upper end portion of the base cylinder portion 19a. The substrate portion 19c protrudes annularly outward in the radial direction from the lower end portion of the base cylinder portion 19a. The lower end edge of the leg cylinder portion 18d of the piston portion 18 is disposed on the upper surface of the substrate portion 19c.

An engaging piece 22 that protrudes upward and enters the annular gap 14 is formed at the outer circumferential edge of the substrate portion 19c. A plurality of engaging pieces 22 are disposed at intervals in the circumferential direction, and the engaging pieces 22 adjacent to each other in the circumferential direction interpose the connections 15 in the circumferential direction. Thus, the relative rotation of the piston support portion 19 to the movable lid portion 6 is restricted.

The packing member 20, for example, is formed of a soft material such as rubber or elastomer, and is formed in an annular shape coaxial with the container axis O. The packing member 20 vertically overlaps the piston support portion 19, and the upper surface thereof comes into contact with the lower surface of the substrate portion 19c and is fixed. Accordingly, the packing member 20 is disposed between the lid base portion 5 and the upper end opening edge of the mouth portion 2b of the container body 2.

In the packing member 20, an annular protrusion 20a protruding downward is formed on the lower surface thereof, and a crushing protrusion 20b protruding downward is formed outside the annular protrusion 20a. Further, on the upper surface of the packing member 20, an overhang recess 20c is formed so as to be partially located just above the crushing protrusion 20b. Further, an inner protrusion 20d protruding inward in the radial direction is formed on the inner circumferential surface of the packing member 20.

The annular protrusion 20a suppress the crushing protrusion 20b from being deformed inward in the radial direction, when the crushing protrusion 20b is relatively pressed against the guide cylinder 4 to be described later.

Figure 2A:
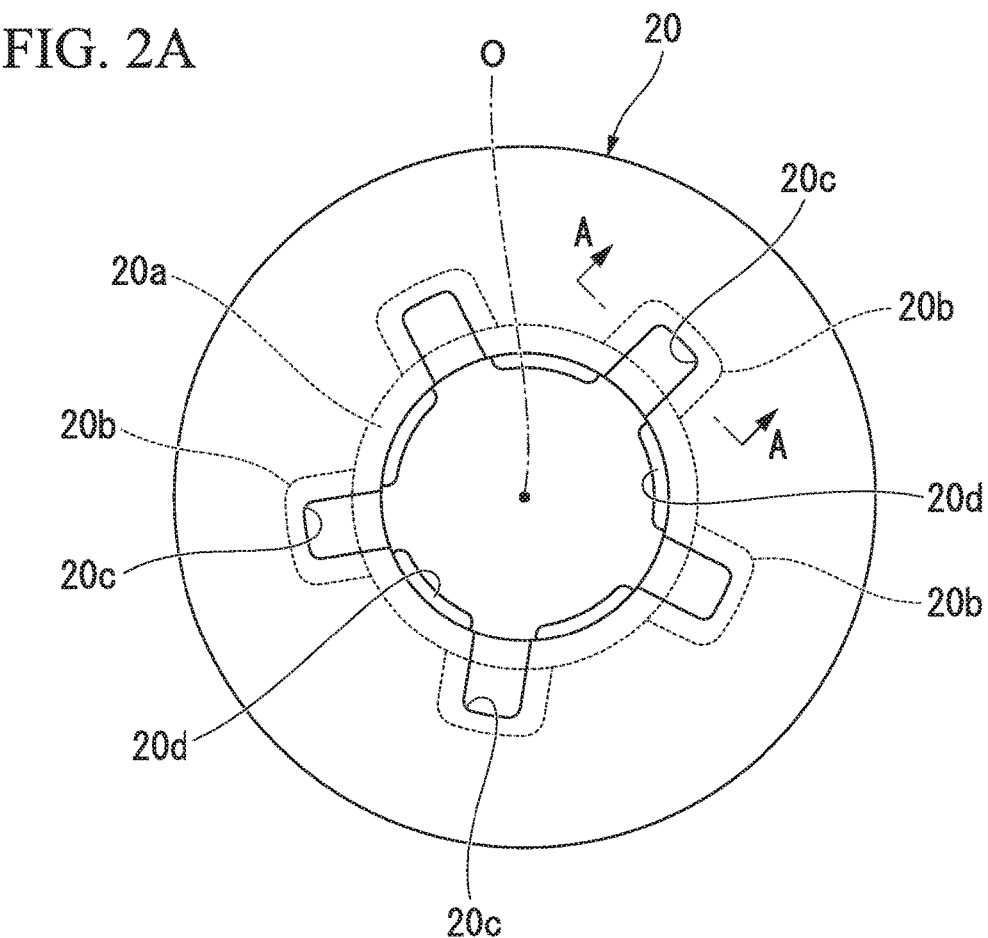
FIG. 2A is a plan view of a packing member.
Figure 3:
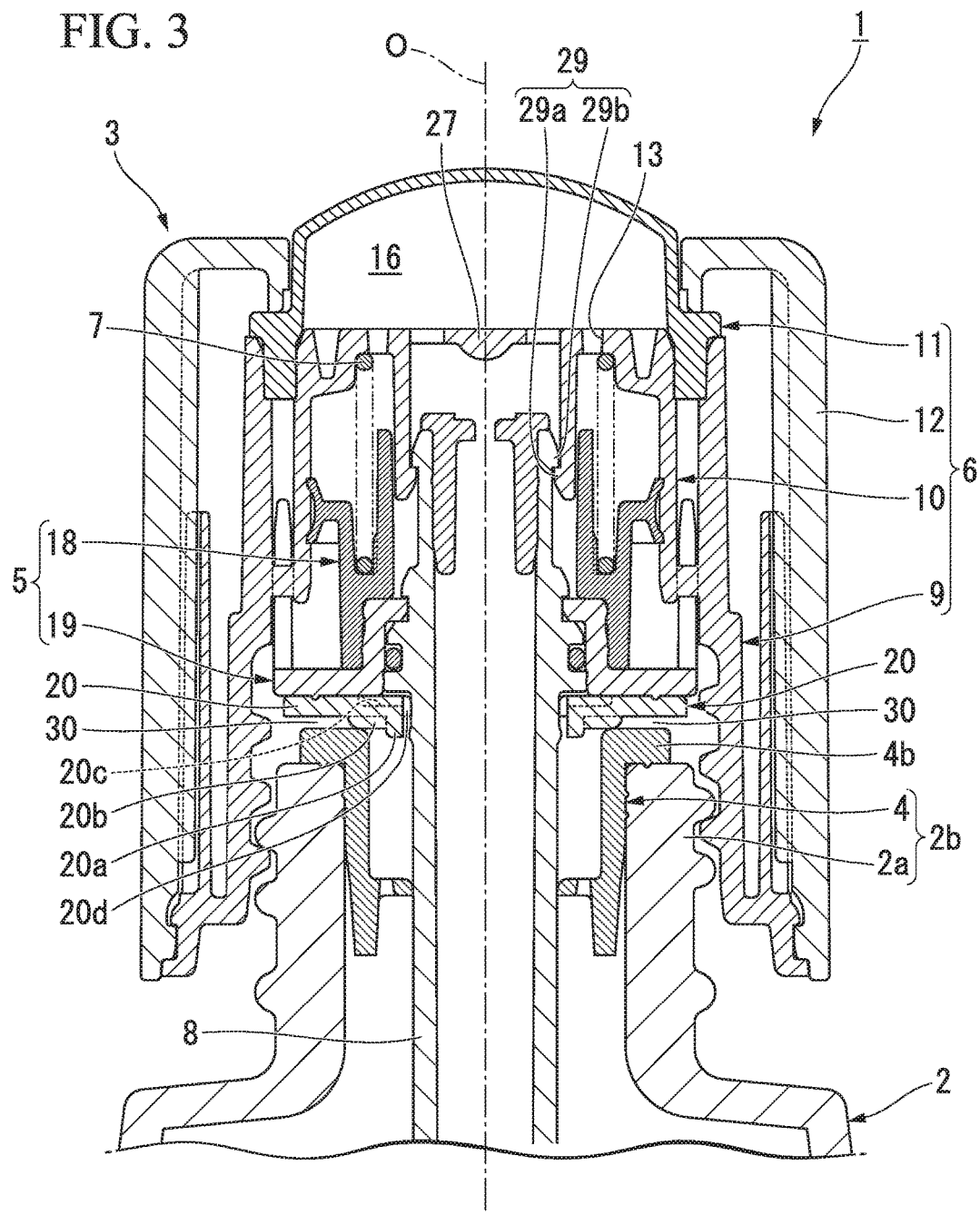
FIG. 3 is a vertical sectional view of main parts of the syringe container shown in FIG. 1, showing a state in which the movable lid portion is open.
Figure 4:
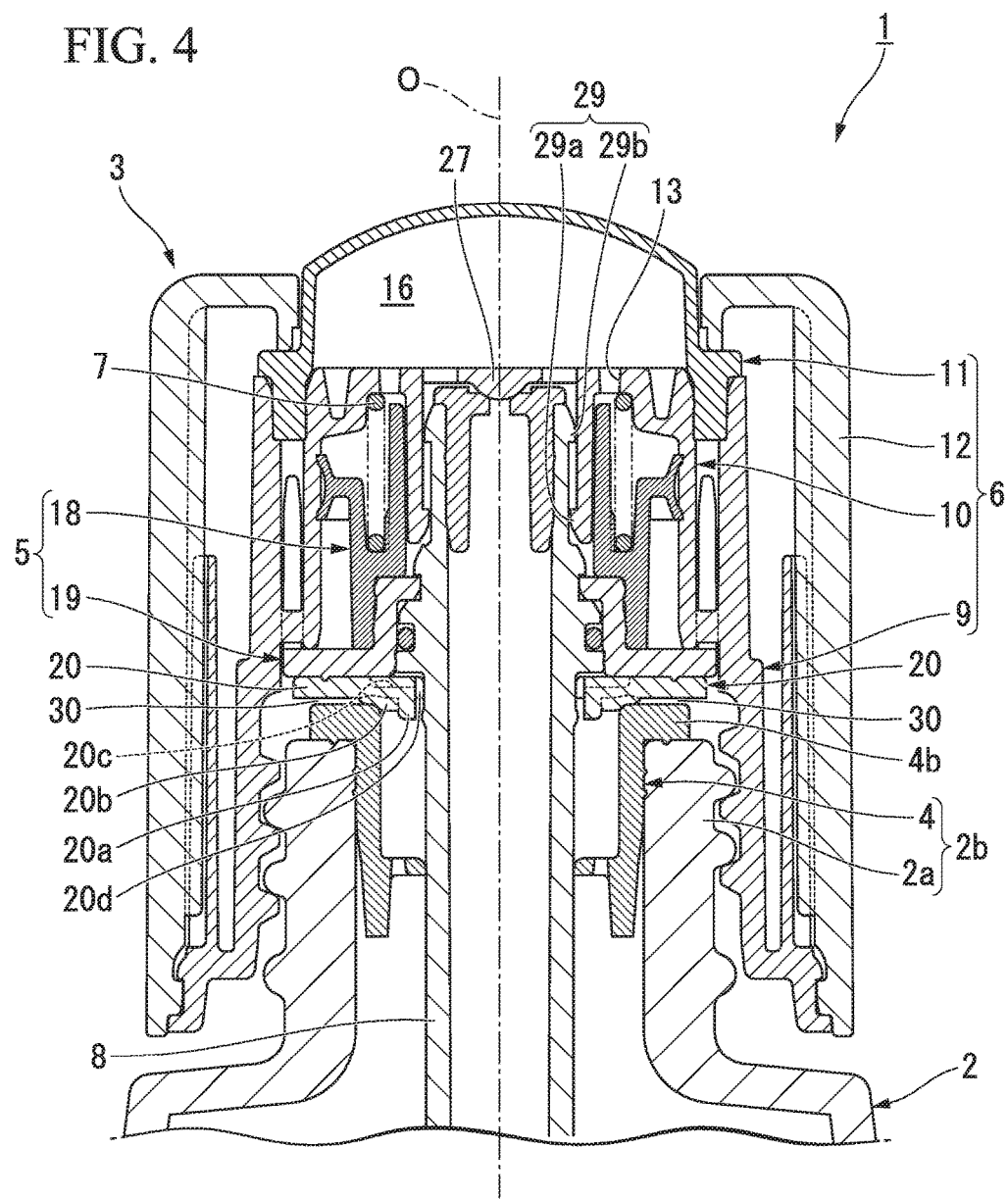
FIG. 4 is a vertical sectional view of main parts of the syringe container shown in FIG. 1, showing a state in which the movable lid portion is closed.

As shown in FIGS. 3 and 4, the crushing protrusion 20b is disposed so which a portion located on the outer side in the radial direction comes into contact with the upper end opening edge of the guide cylinder 4. In this embodiment, as shown by the broken line in FIG. 2A, the five crushing protrusions 20b are formed on the inner circumferential edge portion of the annular packing member 20 at equal intervals in the circumferential direction. However, the number of crushing protrusions 20b is not limited to five, and any number of crushing protrusions 20b may be formed. Further, in the present embodiment, the thickness of the crushing protrusion 20b in the vertical direction is thinner than which of the annular protrusion 20a as shown in FIGS. 3 and 4.

Figure 2B:
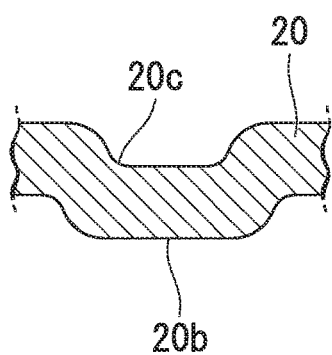
FIG. 2B is a cross-sectional view taken along a line A-A of FIG. 2A.

The overhang recess 20c is formed so which a portion thereof is located just above the crushing protrusion 20b and the remaining portions are located just above the annular protrusion 20a as shown in FIG. 2A, and as shown in FIG. 2B which is a cross-sectional view taken along a line A-A of FIG. 2A, the overhang recess 20c is formed with a recessed amount (recessed depth) which is substantially equal to the protruding amount (protruding height) of the crushing protrusion 20b. Such an overhang recess 20c functions to allow the deformation of the crushing protrusion 20b or a circumferential edge portion thereof such which the deformation of the crushing protrusion 20b is not impeded, when the crushing protrusion 20b is relatively pressed against the guide cylinder 4 and crushed as described later.

Further, in this embodiment, as shown in FIG. 2A, the crushing protrusion 20b is longer than the overhang recess 20c in a radially outward direction, and its width is formed to be wider in the circumferential direction.

The inner protrusion 20d suppresses the displacement of the packing member 20 to the syringe tube 8 side caused when the crushing protrusion 20b is relatively pressed against the guide cylinder 4 as described later and the pressing force is directed in the radially inward direction of the packing member 20, by the inner circumferential surface of the inner protrusion 20d coming into contact with the outer circumferential surface of the syringe tube 8.

The cylinder portion 10 of the movable lid portion 6 is mounted on the syringe tube 8 to freely rise, and the syringe tube 8 is connected to the lid base portion 5. The upper end portion of the syringe tube 8 is inserted into the movable lid portion 6 and the lid base portion 5. The outer diameter of the upper end portion of the syringe tube 8 gradually enlarges in a stepwise manner from the upper side toward the lower side, and a small-diameter tube portion 23, a middle-diameter tube portion 24 and a large-diameter tube portion 25 are formed in the upper end portion of the syringe tube 8.

The small-diameter tube portion 23 is inserted into the inner circumferential wall 10b of the cylinder portion 10 to be freely vertically movable. In the middle-diameter tube portion 24, a fitting groove 24a to which the annular plate portion 19b of the piston support portion 19 is fitted is circumferentially provided. The large-diameter tube portion 25 is fitted into the base cylinder portion 19a of the lid base portion 5, and is located just above the packing member 20. In the large-diameter tube portion 25, a ring holding groove 25a to which an O-ring 26 is fitted is circumferentially provided. The O-ring 26 forms an airtight seal between the large-diameter tube portion 25 and the base cylinder portion 19a.

Further, in the shown example, in the inner circumferential wall 10b of the cylinder portion 10, a valve body 27 that closes the upper end opening of the syringe tube 8 in a freely opening and closing manner is provided. The valve body 27 is disposed on the container axis O, and is connected to the upper end portion of the inner circumferential wall 10b of the cylinder portion 10 via bridge portions 28. A plurality of bridge portions 28 are disposed at intervals in the circumferential direction. When the movable lid portion 6 rises to the syringe tube 8, and the upper end opening of the syringe tube 8 is opened by the valve body 27, the interior of the syringe tube 8 communicates with the space 16. That is, the interior of the syringe tube 8 can communicate with the space 16.

The syringe tube 8 and the cylinder portion 10 are formed with engaging portions 29 which engage with each other when the cylinder portion 10 is located at the rising end position to the syringe tube 8. As the engaging portion 29, an outer engaging portion 29a provided in the cylinder portion 10, and an inner engaging portion 29b provided on the syringe tube 8 are provided. The outer engaging portion 29a annularly protrudes inward in the radial direction from the lower end of the inner circumferential wall 10b of the cylinder portion 10, and the inner engaging portion 29b annularly protrudes outward in the radial direction from the upper end of the small-diameter tube portion 23 of the syringe tube 8. The outer engaging portion 29a faces the inner engaging portion 29b from the lower part, and when the cylinder portion 10 rises to the syringe tube 8, the outer engaging portion 29a engages with the inner engaging portion 29b from the lower part, thereby restricting further rising movement of the cylinder portion 10.

The urging means 7 is disposed between the cylinder portion 10 of the movable lid portion 6 and the piston portion 18 of the lid base portion 5. The urging means 7 is supported by the top wall portion 10c of the cylinder portion 10 from the upper part, and is supported on the bottom wall portion 18c of the piston portion 18 from the lower part. The urging means 7 is formed in a cylindrical shape, and is disposed coaxially with the container axis O. As the urging means 7, for example, a coil spring or the like can be adopted.

In the syringe container 1, as shown in FIG. 1, in the initial state in which the syringe cap 3 is mounted to the container body 2, the packing member 20 is pressed against the flange portion 4b of the guide cylinder 4 in the mouth portion 2b of the container body 2. That is, the packing member 20 is sandwiched between the lid base portion 5 and the upper end opening edge of the mouth portion body 2a of the container body 2 via the flange portion 4b. At this time, when the packing member 20 is pressed against the flange portion 4b, the crushing protrusion 20b is crushed to an upper end opening edge of the mouth portion 2b. Thus, the packing member 20 comes into contact with the flange portion 4b without a clearance to provide a good seal between the lid base portion 5 and the flange portion 4b, i.e., between the lid base portion 5 and the upper end opening edge of the mouth portion 2b of the container body 2, thereby air-tightly closing the mouth portion 2b.

Further, by forming the overhang recess 20c just above the crushing protrusion 20b, the elastic deformation of the packing member 20 caused by crushing of the crushing protrusion 20b is allowed without impeding the elastic deformation, and the elastic deformation easily occurs.

Next, the operation of the syringe container will be described.

When spouting the contents, first, in order to disengage the syringe cap 3 from the container body 2, the screwing between the mounting cylinder 9 of the movable lid portion 6 and the mouth portion body 2a of the container body 2 is released, and the movable lid portion 6 is raised with respect to the container body 2. At this time, when the external cylinder 12 of the movable lid portion 6 is rotated to the loosened side around the container axis O with respect to the container body 2, the rotational force is transmitted to the mounting cylinder 9 via the rotation restricting portion 17 and the engagement cylinder 9d, the mounting cylinder 9 rotates with the external cylinder 12, and the entire movable lid portion 6 rotates. Furthermore, in this embodiment, when the connection 15 of the movable lid portion 6 engages with the engaging piece 22 of the substrate portion 19c at this time, the lid base portion 5 also rotates with the movable lid portion 6.

When rotating the movable lid portion 6 to the loosened side around the container axis O and raising the movable lid portion 6 with respect to the container body 2, due to the urging force of the urging means 7, the piston portion 18 of the lid base portion 5 slides relatively downward inside the cylinder portion 10 of the movable lid portion 6, the internal volume of the cylinder portion 10 increases, and the valve body 27 opens the upper end opening of the syringe tube 8, while a negative pressure is generated in the cylinder portion 10. The negative pressure generated in the cylinder portion 10 is exerted on the container body 2 through the communication hole 13, the space 16 and the syringe tube 8, and the contents of the container body 2 are sucked into the syringe tube 8.

As shown in FIG. 3, the movable lid portion 6 rises to a rising end position with respect to the syringe tube 8, and the engaging portions 29 (the outer engaging portions 29a, and the inner engaging portions 29b) are engaged with each other. After that, when the movable lid portion 6 is further raised to the container body 2, the movable lid portion 6 and the syringe tube 8 rise together via the engaging portion 29. Thus, the syringe tube 8 is extracted from the container body 2, and the syringe cap 3 is detached from the container body 2. At this time, because the pressing force of the packing member 20 to the crushing protrusion 20b is released, the crushing protrusion 20b is restored and deformed into a protruding shape.

Further, by pressing the film cylinder portion 11b of the lid 11 in the syringe cap 3 that is detached from the container body 2, the contents of the syringe tube 8 are spouted from the lower end opening of the syringe tube 8.

When the syringe cap 3 detached from the container body 2 is mounted again, by inserting the syringe tube 8 into the mouth portion 2b of the container body 2 via the movable lid portion 6, and for example, by rotating the external cylinder 12 to the tightened side around the container axis O to the container body 2 to screw the mounting cylinder 9 to the mouth portion body 2a, the movable lid portion 6 is lowered to the container body 2.

At this time, when inserting the syringe tube 8 into the mouth portion 2b of the container body 2, as shown in FIG. 3, the packing member 20 below the lid base portion 5 is placed on the flange portion 4b of the guide cylinder 4. However, since the pressing force of lowering the lid base portion 5 is hardly applied, the packing member 20 maintains a protruding state without crushing of the crushing protrusion 20b. Thus, a communication gap 30 is formed between the packing member 20 and the flange portion 4b.

Further, when the movable lid portion 6 is lowered to the container body 2 from the state shown in FIG. 3 as shown in FIG. 4, the cylinder portion 10 is lowered against the urging force of the urging means 7, and the lid base portion 5 is also pressed downward accordingly. Then, the pressing force of lowering the lid base portion 5 acts on the packing member 20, and the crushing protrusion 20b of the packing member 20 is gradually crushed. However, until the crushing protrusion 20b is sufficiently crushed, the communication gap 30 between the packing member 20 and the flange portion 4b is ensured without being closed.

When the movable lid portion 6 is lowered to the lid base portion 5 to reach the state shown in FIG. 4 from the state shown in FIG. 3, the piston portion 18 of the lid base portion 5 slides relatively upward inside the cylinder portion 10 of the movable lid portion 6 to reduce the internal volume of the cylinder portion 10 and generate a positive pressure in the cylinder portion 10. The positive pressure is exerted on the interior of the container body 2 via the communication hole 13, the space 16 and the syringe tube 8. At this time, since the interior of the container body 2 communicates with the exterior through the communication gap 30, the positive pressure exerted on the interior of the container body 2 is released to the exterior through the communication gap 30, and the internal pressure rise in the container body 2 is suppressed.

After that, by further lowering the movable lid portion 6, the syringe cap 3 is lowered to the container body 2. Thus, as shown in FIG. 1, the lid base portion 5 presses the packing member 20 to crush the crushing protrusion 20b, and closes the communication gap 30 between the packing member 20 and the flange portion 4b. Thus, sealing properties between the packing member 20 and the flange portion 4b are ensured.

When spouting the contents again, the screwing of the mounting cylinder 9 to the mouth portion body 2a is released again, and the movable lid portion 6 is raised to the container body 2. Since the internal pressure rise in the container body 2 is suppressed at the time of the previous spouting operation, when a negative pressure is generated in the cylinder portion 10 at the time of the present spouting operation, a certain amount of contents of the container body 2 is accurately sucked into the syringe tube 8. If the positive pressure generated in the cylinder portion 10 at the time of the previous spouting operation is not released to the exterior, the degree of increase in internal pressure of the container body 2 based on the positive pressure changes according to the remaining amount of the contents. Accordingly, when a negative pressure is generated in the cylinder portion 10 at the time of the present spouting operation, even if the magnitude of the negative pressure is the same, there is a possibility of change in the suction amount of the contents to the syringe tube 8.

As described above, according to the syringe container 1 of the present embodiment, when the movable lid portion 6 is lowered to the lid base portion 5, the positive pressure generated in the cylinder portion 10 is released to the exterior through the communication gap 30 formed by the crushing protrusion 20b of the packing member 20, thereby making it possible to suppress an increase in internal pressure of the container body 2. Therefore, it is possible to keep the suction amount constant with high precision, regardless of the remaining amount of the contents.

Further, when the mounting cylinder 9 rotates about the container axis O, the lid base portion 5 engages with the connection 15 and rotates with the movable lid portion 6. Accordingly, when the mounting cylinder 9 is attached to or detached from the mouth portion 2b of the container body 2, it is also possible to rotate the lid base portion 5 as well as the movable lid portion 6. Accordingly, it is possible to allow the piston portion 18 to smoothly slide vertically inside the cylinder portion 10.

Further, the external cylinder 12 exposes the lid 11 upward, while interposing the circumferential edge portion thereof in the vertical direction between the mounting cylinder 9 and the external cylinder 12. Therefore, it is possible to firmly fix the lid 11 to the mounting cylinder 9, without impeding the pressing operation of the lid 11.

Further, in the present embodiment, the valve body 27 closes the upper opening of the syringe tube 8 in the initial state. Thus, for example, even when unintentionally operating the lid 11 in the initial state, it is possible to suppress the contents in the container body 2 from accidentally flowing into the syringe tube 8. Therefore, it is possible to keep the spouting amount of contents from the syringe tube 8 constant with high accuracy. Further, for example, even if the contents of the container body 2 flow into the syringe tube 8 due to the turnover of the syringe container 1 in the initial state, it is possible to block the contents by the valve body 27. Therefore, it is also possible to restrict the contents from flowing into the space 16.

Second Embodiment

Next, a syringe container according to a second embodiment of the present invention will be described.

In the second embodiment, the same components as the in the first embodiment are denoted by the same reference numerals, the description thereof will not be provided, and only differences will be described.

Figure 5:
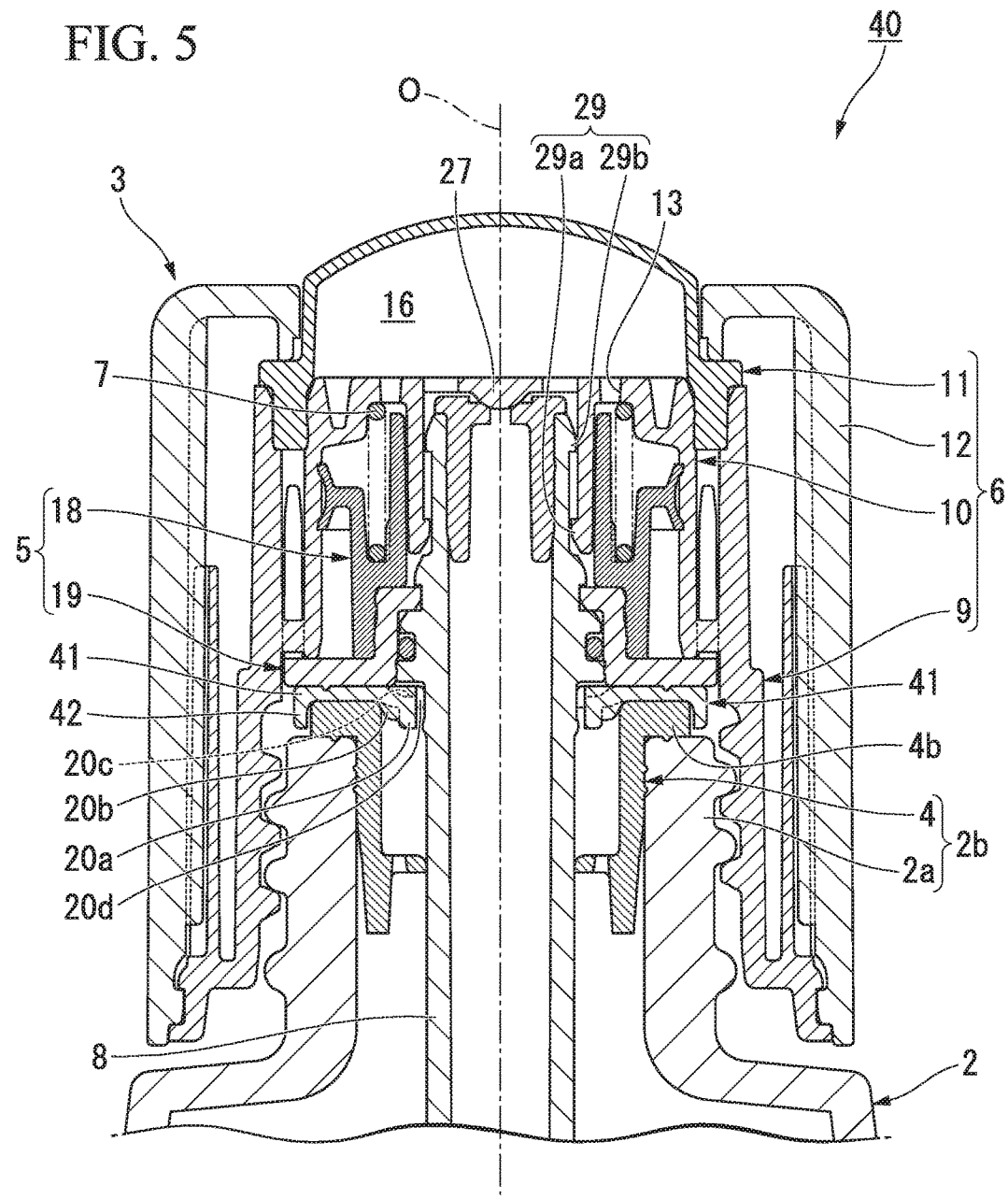
FIG. 5 is a vertical sectional view of main parts of a syringe container according to a second embodiment of the present invention, showing an initial state.

As shown in FIG. 5, in the syringe container 40 of the present embodiment, in addition to the configuration shown in FIGS. 1 and 2, the packing member 41 forms a locking protrusion 42 in the outer circumferential edge portion. The locking protrusion 42 is formed in a cylindrical shape in this embodiment, and engages with the outer circumferential surface of the upper end opening portion of the mouth portion 2b of the container body 2, i.e., the outer circumferential surface of the flange portion 4b of the guide cylinder 4 in an engageable and disengageable manner. However, the locking protrusion 42 may not be formed in a cylindrical shape, and a plurality of protruding pieces may be disposed and formed on the outer circumference at predetermined intervals.

By including the packing member 41 formed with such a locking protrusion 42, in the syringe container 40 of the present embodiment, after spouting the contents from the syringe tube 8, when the movable lid portion 6 is mounted to the container body 2 again, and the movable lid portion 6 is lowered, the displacement of the packing member 41 to the interior of the container body 2 caused by being crushed between the lid base portion 5 and the upper end opening edge of the mouth portion 2b of the container body 2 is suppressed by the locking protrusion 42 which engages with the outer circumferential surface (the outer circumferential surface of the flange portion 4b of the guide cylinder 4) of the upper end opening portion of the container body 2.

Therefore, in the syringe container 40 of the present embodiment, it is possible to satisfactorily ensure the sealing properties of the packing member 41, and it is possible to suppress the deformation and deterioration of the packing member 41 associated with the long period of use. Further, as in the first embodiment, when the movable lid portion 6 is lowered to the lid base portion 5, because the positive pressure generated in the cylinder portion 10 is released to the exterior and an internal pressure rise in the container body 2 can be suppressed, it is possible to keep the suction amount constant with high precision, regardless of the remaining amount of the contents.

The technical scope of the present invention is not limited to the above embodiments, and it is possible to apply various changes without departing from the gist of the present invention.

For example, the mounting cylinder 9 may not be screwed to the mouth portion body 2a of the container body 2. That is, the present invention can be appropriately changed to another form in which the mounting cylinder 9 is mounted on the mouth portion 2b in a freely attachable and detachable manner It is possible to appropriately replace the components of the embodiment with well-known components within the scope which does not depart from the gist of the present invention, and the aforementioned modified examples may be appropriately combined.

INDUSTRIAL APPLICABILITY

According to the present invention, it is possible to provide a syringe container in which the suction amount is kept constant with high precision, regardless of the remaining amount of the contents.

REFERENCE SIGNS LIST

1 Syringe container
2 Container body
2b Mouth portion
5 Lid base portion
6 Movable lid portion
7 Urging means
8 Syringe tube
9 Mounting cylinder
10 Cylinder portion
11 Lid
12 External cylinder
13 Communication hole
15 Connection
16 Space
18 Piston portion
20 Packing member
20b Crushing protrusion
20c Overhang recess
29 Engaging portion
40 Syringe container
41 Packing member
42 Locking protrusion
O Container axis

What is claimed is:

1. A syringe container comprising:
a container body which stores contents;
a lid base portion which is disposed on a mouth portion of the container body;
a movable lid portion which is disposed to freely move upward to the lid base portion;
an urging means which urges the lid base portion and the movable lid portion in a vertically separating direction; and
a syringe tube which is mounted on the lid base portion and extends toward the container body;
the movable lid portion including:
  a mounting cylinder which is mounted on the mouth portion of the container body in a freely attachable and detachable manner,
  a lid which is formed to be elastically deformable and closes an upper end opening of the mounting cylinder, and
  a cylinder portion which is disposed inside the mounting cylinder in a radial direction and is connected to the mounting cylinder;
the lid base portion including a piston portion which is connected to the syringe tube and is fitted to the inside of the cylinder portion to freely slide up and down;
the cylinder portion being mounted on the syringe tube to freely rise, and the cylinder portion and the syringe tube being formed with engaging portions which engage with each other when the cylinder portion is located at a rising end position with respect to the syringe tube;
an interior of the syringe tube communicating with a space between the upper end opening of the mounting cylinder and the lid;
the cylinder portion being formed with a communication hole through which the interior and the space communicate with each other;
wherein a packing member is disposed between the lid base portion and an upper end opening edge of the mouth portion of the container body, and
a crushing protrusion is formed on a lower surface of the packing member, the crushing protrusion protruding downward and being crushed to an upper end opening edge of the container body, and an overhang recess is formed on an upper surface of the packing member, the overhang recess being at least partially located just above the crushing protrusion.

2. The syringe container according to claim 1, wherein the packing member is formed with a locking protrusion which is locked with an outer circumferential surface of the upper end opening of the mouth portion of the container body.

3. The syringe container according to claim 2, wherein the mounting cylinder is screwed into the mouth portion, and is connected to the cylinder portion via a connection, and
the lid base portion engages with the connection when the mounting cylinder rotates about a container axis, and rotates with the movable lid portion.

4. The syringe container according to claim 3, wherein the movable lid portion comprises an external cylinder which is mounted on the mounting cylinder to be relatively vertically immovable and non-rotatable from an outside in a radial direction, and
the external cylinder exposes the lid upward, while interposing a circumferential edge portion of the lid in the vertical direction between the mounting cylinder and the external cylinder.

5. The syringe container according to claim 2, wherein the movable lid portion comprises an external cylinder which is mounted on the mounting cylinder to be relatively vertically immovable and non-rotatable from an outside in a radial direction, and
the external cylinder exposes the lid upward, while interposing a circumferential edge portion of the lid in the vertical direction between the mounting cylinder and the external cylinder.

6. The syringe container according to claim 1, wherein the mounting cylinder is screwed into the mouth portion, and is connected to the cylinder portion via a connection, and
the lid base portion engages with the connection when the mounting cylinder rotates about a container axis, and rotates with the movable lid portion.

7. The syringe container according to claim 6, wherein the movable lid portion comprises an external cylinder which is mounted on the mounting cylinder to be relatively vertically immovable and non-rotatable from an outside in a radial direction, and the external cylinder exposes the lid upward, while interposing a circumferential edge portion of the lid in the vertical direction between the mounting cylinder and the external cylinder.

8. The syringe container according to claim 1, wherein the movable lid portion comprises an external cylinder which is mounted on the mounting cylinder to be relatively vertically immovable and non-rotatable from an outside in a radial direction, and the external cylinder exposes the lid upward, while interposing a circumferential edge portion of the lid in the vertical direction between the mounting cylinder and the external cylinder.

* * * * *